(12) United States Patent
Bergagnoli

(10) Patent No.: US 8,882,842 B2
(45) Date of Patent: Nov. 11, 2014

(54) MODULAR PROSTHESES AND METHOD FOR THE IMPLANTATION OF MODULAR PROSTHESES

(75) Inventor: Rudolf Bergagnoli, Straubing (DE)

(73) Assignee: Global Medical Consulting GmbH, Bogen (DE)

( * ) Notice: Subject to any disclaimer, the term of this patent is extended or adjusted under 35 U.S.C. 154(b) by 366 days.

(21) Appl. No.: 12/741,358

(22) PCT Filed: Nov. 6, 2008

(86) PCT No.: PCT/DE2008/001831
§ 371 (c)(1),
(2), (4) Date: May 4, 2010

(87) PCT Pub. No.: WO2009/071045
PCT Pub. Date: Jun. 11, 2009

(65) Prior Publication Data
US 2010/0256762 A1    Oct. 7, 2010

(30) Foreign Application Priority Data

Dec. 4, 2007    (DE) .................... 10 2007 058 301

(51) Int. Cl.

| A61F 2/44 | (2006.01) |
|---|---|
| A61B 17/70 | (2006.01) |
| A61F 2/08 | (2006.01) |
| A61F 2/30 | (2006.01) |
| A61F 2/46 | (2006.01) |

(52) U.S. Cl.
CPC ............. *A61F 2/442* (2013.01); *A61B 17/7062* (2013.01); *A61F 2/4425* (2013.01); *A61F 2/4455* (2013.01); *A61F 2/08* (2013.01); *A61F 2002/30387* (2013.01); *A61F 2002/30426* (2013.01); *A61F 2002/30433* (2013.01); *A61F 2002/30563* (2013.01); *A61F 2002/30566* (2013.01); *A61F 2002/30607* (2013.01); *A61F 2002/30614* (2013.01); *A61F 2002/30649* (2013.01); *A61F 2002/30662* (2013.01); *A61F 2002/443* (2013.01); *A61F 2002/4631* (2013.01); *A61F 2220/0025* (2013.01); *A61F 2220/0041* (2013.01); *A61F 2250/0062* (2013.01)
USPC ...................... 623/17.16; 623/17.11

(58) Field of Classification Search
USPC ........................................ 623/17.16
See application file for complete search history.

(56) References Cited

U.S. PATENT DOCUMENTS 5,674,296 A    10/1997    Bryan et al.
2003/0204261 A1    10/2003    Eisermann et al.
(Continued)

FOREIGN PATENT DOCUMENTS

| DE | 695 16 603 | 3/2001 |
|---|---|---|
| WO | WO2005/027800 | 3/2005 |
| WO | WO 2005/094732 | 10/2005 |
| WO | WO2007/003438 | 1/2007 |

*Primary Examiner* — Andrew Yang
*Assistant Examiner* — Olivia C Chang
(74) *Attorney, Agent, or Firm* — Jennifer S. Stachniak; Rober W. Becker

(57) ABSTRACT

A method of implanting an intervertebral disk prosthesis, and a modular intervertebral disk prosthesis. The method includes permanently anchoring at least one apposition plate with respective vertebra bodies and detachably connecting an intermediate module with the apposition plate such that the intermediate module can be removed and replaced postoperatively. The modular prosthesis includes at least one apposition plate configured to be permanently implanted, and an intermediate module configured to be detachably secure to the apposition plate.

5 Claims, 3 Drawing Sheets

(56) References Cited

U.S. PATENT DOCUMENTS

| | | |
|---|---|---|
| 2005/0049707 A1 | 3/2005 | Ferree |
| 2005/0187631 A1* | 8/2005 | Van Hoeck et al. ........ 623/17.13 |
| 2005/0228500 A1* | 10/2005 | Kim et al. .................. 623/17.13 |
| 2007/0073311 A1 | 3/2007 | Williams et al. |
| 2007/0250173 A1* | 10/2007 | Berry et al. ................ 623/17.16 |
| 2008/0195206 A1* | 8/2008 | Chee et al. ................ 623/17.11 |

* cited by examiner

MODULAR PROSTHESES AND METHOD FOR THE IMPLANTATION OF MODULAR PROSTHESES

The instant application should be granted the priority dates of Dec. 4, 2007, the filing date of the corresponding German patent application 10 2007 058 301.1, as well as Nov. 6, 2008, the filing date of the International patent application PCT/DE2008/001831.

BACKGROUND OF THE INVENTION

The present invention relates to a method for the implantation of modular prostheses. The invention also relates to a modular prosthesis.

Modular prostheses are known. DE 695 16 603 T2, WO 2005/027800 A2, and WO 2005/094732 A1 describe, by way of example, intervertebral disk prostheses having a modular construction. Pursuant to WO 2005/094732 A1, the modular prosthesis, in the form of an assembly of prefabricated parts composed of a number of intermediate pieces and a number of vertebra end plates or vertebra end plates of different construction for the pertaining patient and detachably secured thereon, is preoperatively assembled and then implanted. If necessary, an exchange of modules also takes place interoperatively if the anatomical conditions of the patient require this. Involved in this connection is the suitable assembly of the prosthesis modules prior to or also during the surgical operation.

However, situations frequently occur in which the operation must be repeated due to wear or destruction of the implant, or for other reasons, and possibly after many years. The implantation of prostheses is a complicated operation. It is therefore an object of the present invention to provide a method and a prosthesis of the aforementioned general type that make it possible to simplify the surgical operation, especially during follow-on or subsequent operations.

SUMMARY OF THE INVENTION

The object is inventively realized by a method of implanting an intervertebral disk prosthesis that includes the steps of permanently anchoring at least one apposition plate with respective vertebra bodies, and detachably connecting an intermediate module with the at least one apposition plate such that the intermediate module can be removed and replaced postoperatively. The object is also inventively realized by a modular intervertebral disk prosthesis that comprises at least one apposition plate configured to be permanently implanted and an intermediate module configured to be detachably secured to the at least one apposition plate. Accordingly, at least one module of the implant is configured and implanted in such a way that it is permanently fixed on bones in the human body, and thus serves as a support for the remaining, replaceable modules of the prosthesis, which are the actual functional modules. This means that the replaceable prosthesis modules, which replace a function in the body, are connected to a fixedly anchored support module, which takes place with current means, such as screws, staples, bayonette closures, detachable adhesion, etc. in an again detachable manner. This has the great advantage that if a replacement or exchange of the functional module becomes necessary, it merely needs to be detached from the support module and the new, replaceable module is to be correspondingly attached. In so doing, the bone implant zone remains undisturbed during the repair operation, and the operation does not cause any reduction of the bone substance. Furthermore, a second or third operation can be carried out considerably more rapidly than in the conventional process.

The invention has the further advantage that the permanently to be anchored support module can additionally be utilized for the securement of auxiliary components, such as tension cord bands, shock absorbers, etc., as a result of which a further relief of the bone material is possible.

It is particularly advantageous if the support module which is to be fixedly anchored, as well as the replaceable module components, are standardized. In this way, the surgeon, without having to examine the configuration of the implanted prosthesis, and in particular the module that serves as the support, can from the beginning prepare the appropriate replaceable module and undertake the operation. This avoids the situation where the surgeon notices only during the operation that the prepared replacement module is not compatible with the fixed support module that is introduced in the patient, which would mean a double stressing for the patient since the operation would be unsuccessful and would have to be repeated.

Standardizing has the additional advantage that standardized sets of modular prostheses and auxiliary components, as well as the appropriate instruments for the implantation, can be manufactured economically and the operation can be reduced to a routine operation or intervention.

Appropriate standards are respectively determined for the various prostheses, such as intervertebral disk prostheses, articulated prostheses, and other prostheses, as well as auxiliary components such as shock absorbers, tension cord bands.

In the case of spinal or vertebral column implants, artificial sleeves or casings for spine and transverse extensions, plates or half sleeves for the vertebra curvatures or about the vertebra bodies, as well as nuts or similar blocks as support modules can be used. The artificial vertebra end plates serve for the detachable anchoring of vertebra body implants or intervertebral disk implants, but also at the same time for the support of auxiliary components such as shock absorbers, movement-limitation components, etc. The artificial vertebra end plate replaces the bone material of the vertebra body in that it serves as the anchoring for replaceable functional modules. During a later repair operation, the old artificial vertebra end plates, which remain connected to the natural end plates of the vertebra bodies, are not replaced; rather, they form a mechanically defined component that permits a precise positioning and fixation of replaceable modules, so that during a repair, the surgical operation is essentially reduced or limited to a mechanical replacement or exchange of the functional module. Consequently, the bone anchoring is not disturbed, the bone material is protected, and the operation is considerably shortened.

Due to the fact that during a repair not the entire prosthesis, for example intervertebral disk, vertebra body inner spinal implant, but rather only the functional module and possibly the auxiliary module have to be replaced, significant advantages are obtained, namely that during a repair of the prosthesis for the spine or vertebral column, extensive freedom is provided to the surgeon. The repair operation no longer has to be absolutely carried out from the abdomen or front region of the patient, which due to the temporarily held organs causes complications. The replaceable module can also be conveyed through an access at the side or from the rear of the patient, which means a more protective and complication-free operation on the human body.

Depending upon its use, the replaceable module is configured monolithically, of multiple parts, articulated, as a compression spring, as a cushion, or the like. In each case, the replaceable modules and components are provided with means for the detachable anchoring with one or more artificial support modules. Provided as means for the detachable securement of implant modules are screw connections, dovetailed or bayonette connections or closures, etc. Detachable adhesion is also conceivable.

Likewise, due to its modularity the subject matter of the present invention includes movement modules having different material pairings, dampening characteristics or degrees of freedom of movement. A straightforward embodiment of the artificial vertebra end plates is comprised of two end plates that, equipped with known pins, teeth, etc., are respectively permanently fixed to a vertebra body. Such an embodiment has a low height and thus during insertion requires a smaller intermediate vertebra space and consequently less of an extension of the vertebra body then is the case with conventional total implants. From the beginning, the end plates are equipped with standardized means that serve for the detachable securement of replaceable modules and possibly for the securement of other components, such as tension cord bands, shock absorbers, movement-limitation measures, etc.

The replaceable module is optimally designed to the functions in the body of the patient that are to be replaced, and is similarly provided with means for the anchoring with the vertebra end plates, such as dovetailed counter elements, holes for screws, etc.

A further embodiment of the invention provides for the connection of the replaceable module with a tension cord band, which similarly can be connected with the permanent end plates and serves as part of the intervertebral disk prosthesis for the elastic or fixed movement limitation. With limitations of bending and rotation movabilities of the vertebral column, symmetrical or assymetrical measures or components can be used, or if necessary can be easily altered in that, for example, the movement-limitation components of a pre-implantation are released from the support module and are exchanged for components having different characteristics.

The artificial vertebra end plates are advantageously provided with holes or bores, preferably inclined bores, through which curable material having osteoconductive or osteoinductive properties, or other polymeric materials, can be sprayed into the hollow spaces that remain between the plate and the vertebra body. This compensates for the unevenness of the end surfaces of the vertebra bodies behind the artificial vertebra end plate, so that the introduction of force of the artificial end plate onto the natural vertebra end plate is uniform over the entire contact surface.

Sleeves or casings as fixed platforms are provided for interspinal prostheses or implants. These sleeves or casings, which are open on both ends or only on one end, are placed over spine extensions as well as also transverse extensions, and are similarly permanently fixed on the spine or transverse extension. Standardizing these sleeves or casings offers the same advantages already described above. Sleeves or casings open on the longitudinal sides are used for vertebra curvatures or about the vertebra body.

The present invention can be used with all implants where at least one module is fixedly anchored with bone material and at least one further module can be detachably connected with the first module.

BRIEF DESCRIPTION OF THE DRAWINGS

The invention will be explained in greater detail with the aid of exemplary embodiments schematically illustrated in the drawings, in which.

DESCRIPTION OF SPECIFIC EMBODIMENTS

Figure 1:
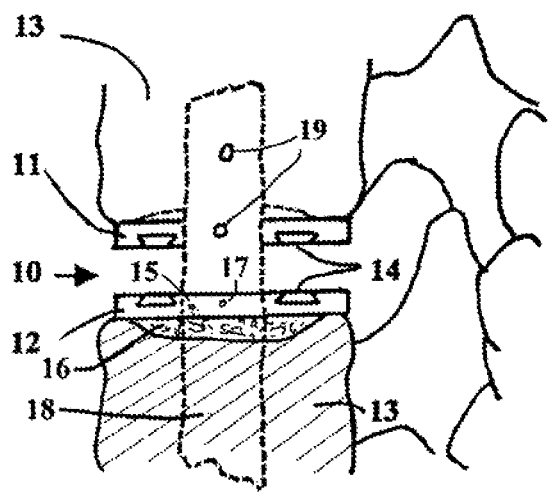
FIG. 1-FIG. 2a show, partially in section, a first exemplary embodiment.

The inventive prosthesis is fundamentally comprised of a support module, which in a first surgical operation is implanted in such a way that it remains permanently anchored in the human body and is configured such that it removably and exchangeably accommodates further modules that represent the actual function of the prosthesis.

In FIGS. 1-5 the invention will be described with the aid of intervertebral disk prostheses that offer a clear overall illustration of the invention. The principle, can, of course, be designed for any prosthesis in a similar manner.

After the removal of the damaged intervertebral disk, a first module, which serves as a support 10 (FIG. 1) and is comprised of two artificial vertebra end plates 11, 12, is inserted and is respectively secured via pins, staples or adhesion with the vertebra bodies 13 in such a way that it remains permanently connected with the vertebra bodies 13. Subsequently, via channels 15 provided in the vertebra end plates 11, 12, curable material that is compatible with the body and has osteoconductive or osteoinductive properties, or some other polymeric material, is sprayed in under the respective artificial vertebra end plates 11, 12 in order to fill the hollow space 16 formed by the approximately concave contact surface of the vertebra body, and to thereby achieve a uniform distribution of pressure. This concludes the preparation for the insertion of the second, i.e. exchangeable or replaceable, module, which assumes the function of the prosthesis.

Figure 2:
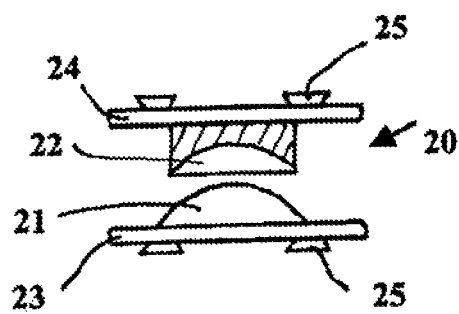

A replaceable or exchangeable module 20 is shown in a longitudinal cross-sectional view in FIG. 2. It is comprised of a hemispherical head 21 and a socket 22 that cooperates with the hemispherical head. These joint or articulation components respectively form a structural unit with a connector part 23, 24. The replaceable module 20 is now inserted between the two artificial vertebra end plates 11, 12 in such a way that the dovetailed elements 25 of the replaceable module 20 engage into the dovetailed grooves 14 of the vertebra end plates 11, 12, thereby effecting a detachable connection between support module 10 and replaceable module 20.

Subsequently, an elastic band or tension cord band 18 is fastened (19) into screw holes 17 of the artificial vertebra end plates 11, 12, and possibly additionally to the vertebra bodies, in order to exert tension forces upon the intervertebral disk prosthesis 10, 20, and at the same time to secure the anchoring of the replaceable module 20. In this connection, the tension cord band also assumes the function of the movement limitation in the bending or flexing direction.

If for example with the patient having the implanted intervertebral disk prosthesis 10, 20 a change is required after a number of years in that the prosthesis must be repaired or replaced, then during a further surgical operation it is merely necessary to unscrew the elastic band 18 and to pull the replaceable module 20 out. The artificial vertebra end plates 11, 12 remain in their original anchored position, and will accommodate a new replaceable module.

Figure 2A:
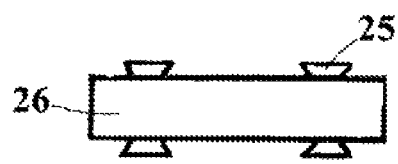

If a repair is provided due to a required reinforcement of the vertebra bodies, then the same technique is undertaken in that instead of an articulated replaceable module, a spacer 26 provided with dovetailed elements 25 (FIG. 2a) is inserted as a replaceable module.

In individual situations, the use of only one artificial vertebra end plate and a replaceable module is possible. In the example of FIGS. 1 and 2, the intervertebral disk prosthesis would be comprised of the vertebra end plate 12, for example in conjunction with the replaceable module component 21, 23; whereby the replaceable module component would rest via the hemispherical head 21 directly in the curvature of the oppositely disposed vertebra body 13.

The invention is independent of the configuration of the modules, in particular of the replaceable module. The vertebra end plates are provided with additional means, such as screw holes 17 or 36 (FIG. 3) that permit the anchoring of other required components, such as support elements, tension cord bands 18, movement-limitation elements, etc.

It is, however, very advantageous if the modules, in particular the support modules that are to be permanently anchored, are standardized. In this way there is nothing in the way of a defined replacement or exchange of functional modules in that the surgeon can, right from the beginning, precisely recognize the support that is anchored in the patient's body. In this connection, it is not absolutely necessary to utilize only unitary functional modules. Their function can readily differ; only their connection to the support module need be standardized and be compatible with the support.

Figure 3:
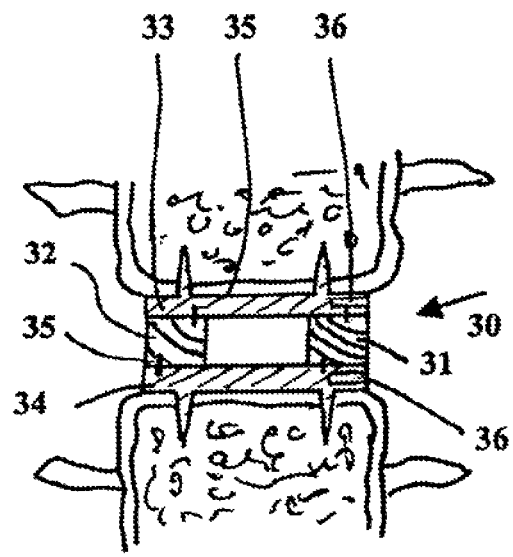
FIG. 3-FIG. 6 each show a further exemplary embodiment in longitudinal section, partial cross-section or plan view.

FIG. 3 shows an example where the replaceable module 30 is comprised of at least two module components 31, 32 that are arranged next to one another. Each of the replaceable module components 31, 32 is comprised of a helix or coil, or interengaging double helixes, the ends of which are respectively fastened or screwed (35) onto the support plates 33, 34 of the first module that are provided with screw holes. The helixes enable tilting movements. This design is suitable for dorsal-sided repair operations. By removing the screws 35, these replaceable module components 31, 32 can be withdrawn and can be replaced by a new replaceable module of the same type or of a different type, by solid blocks in the case of the reinforcement, or elastic blocks. A reinforcement can also be achieved in that after removal of the articulated replaceable module, the two artificial vertebra end plates 33, 34 are directly connected to one another, for example by adhesion or being screwed together.

The design pursuant to FIG. 3 provides the possibility of being able to implant the two replaceable module components 31, 32 from the front, e.g. from the abdominal cavity, during the first operation during which the support plates 33, 34 that are to be permanently inserted are anchored. In contrast, during a second operation the removable module component 31, 32 can be replaced from the rear of the patient.

The example of FIG. 3 is also suitable for the production of intervertebral disk prostheses that enable an assymetrical bending angle in that the replaceable module components 31 and 32 can exert different pressures upon the artificial vertebra end plates 33, 34. A necessary alteration of the bending possibilities is also reason for repair, according to which merely one or both replacement module components 31, 32 have to be replaced by new ones having different spring strengths.

With other articulated prostheses, such as the hemisphere/socket system 21, 22 shown in FIG. 2, bending or flexion limitations having separate means, such as cushions, springs or profiling measures, which are not illustrated yet are known in the state of the art are provided. They can be connected with one or both of the vertebra end plates, or could also be an integral component of a tension cord band. It is often necessary to individually, and in this connection asymmetrically, design the movability limitations for the patient. It is also within the scope of the invention to include these measures in the inventive method. The measures for limiting the flexion-extension movement and/or the lateral bending and/or the rotation about the vertical axis symmetrically or asymmetrically are, just as is the replaceable module, removably integrated or installed into the prosthesis system. If it becomes necessary during the course of time to alter the movement limitations for one or more directions of bending, during the repair operation the pertaining measure is removed from the prosthesis and is replaced with a new one.

Figure 4:
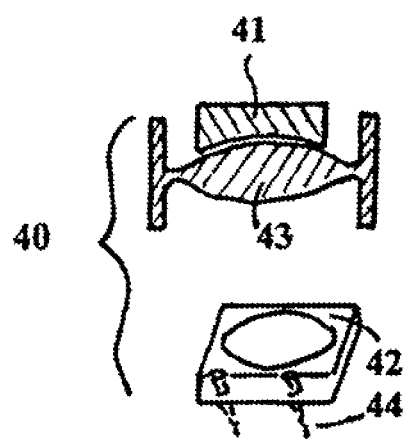

A further example for the replaceable module 40 is schematically illustrated in FIG. 4. It is comprised of three components, namely two cupped elements 41, 42 and a lens-shaped articulation part 43 that is floatingly disposed between the cupped elements 41, 42. This replaceable module 40 is interposed as a loose structural unit between vertebra end plates, such as shown in FIG. 3, and is screwed at an incline to the respective plate via screws 44.

In the example, according to FIG. 4, also possible is the variation where the articulation part 43 is placed directly between two vertebra end plates that are formed with cups. This is one example for a monolithic, articulated replaceable module. In this case, the two cupped elements 41, 42 are formed as vertebra end plates, and are screwed to the respective vertebra bodies via the screws 44.

Figure 5:
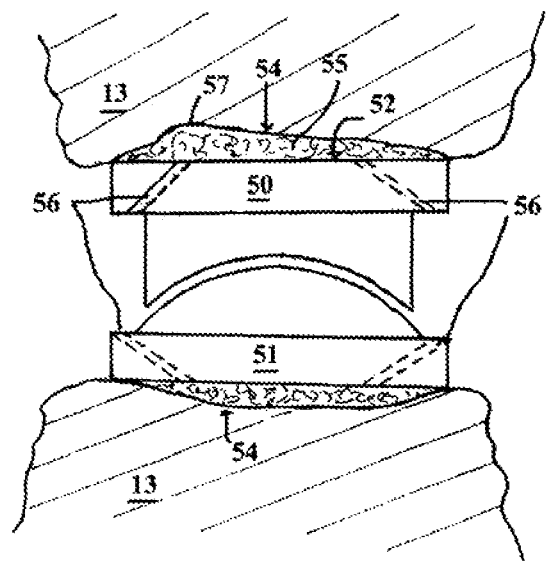

The artificial vertebra end plates 50, 51 pursuant to FIG. 5 generally have planar connection surfaces 52 on the side of the vertebra bodies that are not congruent with the adjoining surfaces 54 of the vertebra body 13, which are most likely concave, in which case hollow spaces 57 remain. As a result, differing pressure conditions result over the surfaces 52, 54 which can rapidly lead to a loosening of the artificial vertebra end plates 50, 51 and/or of the implant. To prevent this, bores or channels 56 are provided in the vertebra end plates 50, 51 through which, after the fixation of the vertebra end plates 50, 51 on the respective vertebra bodies 13, a curable material 55 is sprayed into the intermediate or hollow spaces 57.

Figure 6:
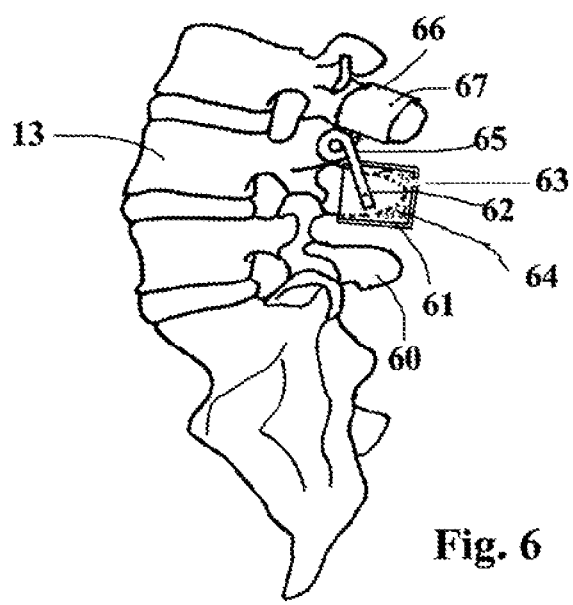

FIG. 6 shows by way of example a support for interspinal prostheses. Illustrated is a spinal or vertebral column in the hip region, seen from the side. The functional module is illustrated as a helical spring 65, the free ends 62 of which are connected with adjoining spine extensions 60. Sleeves or casings 61, 66 are here provided as connection platforms, and are permanently connected to the respective spine extensions 60. The sleeve or casing 66 is open at both ends, and is placed over the spine extension and is fixed thereon via non-illustrated staples, screws or the like. Intermediate spaces between the sleeve or casing 66 and the uneven spine extension surface are filled with a curable material that is sprayed in on the side. The sleeve or casing is provided with means, such as screw holes 67, for the connection of functional modules 65.

The sleeve or casing, which serves as a lasting support, can also be closed off on one side, as the sleeve or casing 61, which is illustrated in the longitudinal section, shows. Here, an opening 63 is provided for spraying the curable material 64 in. Sleeves or casings can also be provided for transverse extensions of vertebra bodies.

The specification incorporates by reference the disclosure of German 10 2007 058 301.1 filed Dec. 4, 2007, as well as International application PCT/DE2008/001831, filed Nov. 6, 2008.

The present invention is, of course, in no way restricted to the specific disclosure of the specification and drawings, but also encompasses any modifications within the scope of the appended claims.

Any body-compatible polymeric or synthetic material can be used as the curable material. Also suitable are materials having osteoconductive or osteoinductive properties.

Sleeve or casing like support modules 61, 66 are also preferably standardized.

The invention claimed is:

1. The use of a modular intervertebral disk prosthesis, said modular intervertebral disk prosthesis comprising at least one apposition plate configured to be permanently implanted, wherein said at least one apposition plate is provided with bores or channels through which a curable material can be sprayed; and a standardized intermediate module configured to be detachably secured to said at least one apposition plate when implanted, wherein said at least one apposition plate is also provided with standardized means for a detachable securement of said standardized intermediate module and auxiliary means to permit a post operative replacement of intermediate modules of the same or different types, including the steps of:

implanting said at least one apposition plate such that said plate or plates is permanently anchored with respective vertebra bodies;

spraying a curable material through a bore or a channel provided in the at least one apposition plate into a hollow space that remains between said at least one apposition plate and an uneven bone surface; and detachably connecting said intermediate module with said at least one apposition plate, wherein during a necessary repair, said intermediate module is postoperatively removed from the at least one apposition plate and replaced.

2. A method according to claim 1, which during a repair operation includes the further steps of removing the existing intermediate module, and connecting a new intermediate module with said at least one apposition plate that was anchored in the initial operation.

3. A method according to claim 1, wherein two apposition plates are permanently anchored with the respective vertebra bodies and wherein during a repair operation for carrying out a reinforcement, the existing intermediate module is removed and said two anchored apposition plates are directly connected to one another.

4. The use of an intervertebral disk prosthesis according to claim 1, wherein said at least one apposition plate is provided with screw holes for the detachable fixation of at least one of said intermediate modules and auxiliary means, including shock absorbers and tension cord bands.

5. The use of an intervertebral disk prosthesis according to claim 1, wherein said at least one apposition plate is configured to be permanently anchored and secured with the vertebral body via pins, staples or adhesion.

* * * * *